(12) United States Patent
Huang

(10) Patent No.: US 8,771,350 B2
(45) Date of Patent: Jul. 8, 2014

(54) AIR-OPERATED SPEECH AID

(76) Inventor: Tong-Yuan Huang, New Taipei (TW)

( * ) Notice: Subject to any disclaimer, the term of this patent is extended or adjusted under 35 U.S.C. 154(b) by 60 days.

(21) Appl. No.: 13/543,828

(22) Filed: Jul. 7, 2012

(65) Prior Publication Data
US 2013/0018462 A1 Jan. 17, 2013

(30) Foreign Application Priority Data

Jul. 15, 2011 (TW) .............................. 100213081 U

(51) Int. Cl.
*A61F 2/20* (2006.01)
*A61M 5/00* (2006.01)

(52) U.S. Cl.
USPC .. 623/9; 623/23.64; 128/200.26; 128/205.24; 128/207.14; 128/207.15; 128/207.16

(58) Field of Classification Search
CPC .......... A61F 2/203; A61F 2/20; A61M 16/04; A61M 5/00
USPC ............................ 623/9, 23.64, 23.65, 23.68; 128/200.26–207.29; 606/108, 606/191–199; 604/8–9
See application file for complete search history.

*Primary Examiner* — David Isabella
*Assistant Examiner* — Yashita Sharma
(74) *Attorney, Agent, or Firm* — Pro-Techtor Int'l Services

(57) ABSTRACT

An air-operated speech aid that includes a cover cup, a tube, a sound guide tube, a gasket, and an internal tube. The cover cup of the speech aid is provided with a breathing hole, and a side of the breathing hole is clasped into a soft air gate. One end of the sound guide tube is encased in a sleeve or a mask type cover member.

2 Claims, 8 Drawing Sheets

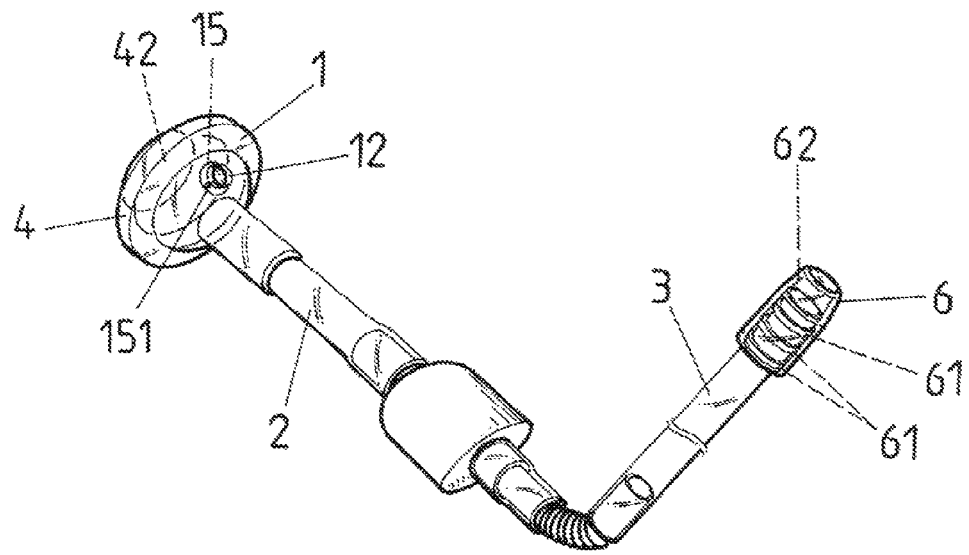
FIG.4
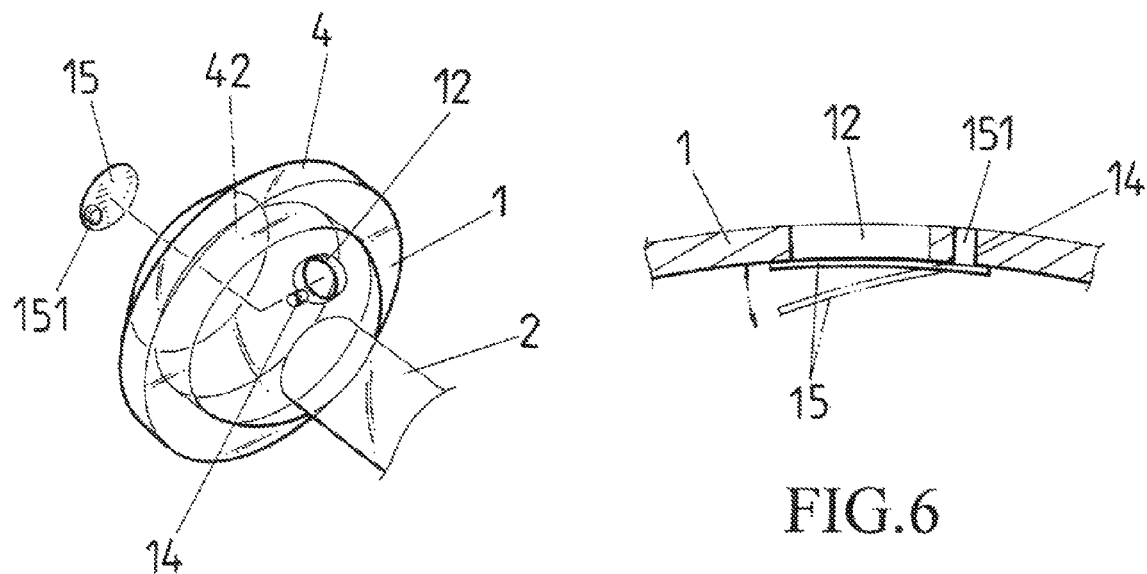
FIG.5
FIG.6

AIR-OPERATED SPEECH AID

BACKGROUND OF THE INVENTION (a) Field of the Invention

The present invention relates to an air-operated speech aid, and more particularly to a multifunctional speech aid.

(b) Description of the Prior Art

Referring to FIG. 9, in most cases, for a patient suffering from a general throat malignant tumor or throat cancer, the lesions produced in the larynx (throat) 100 are removed, and, for the patient to emit sound, the patient must undergo additional surgery to create a new stoma 201 that connects a disconnected larynx 100 to a trachea 400 of lungs 300. Referring to FIG. 12, a cover cup 501 of a speech aid 500 is used to to cover the surgically created new stoma 201. The fingers are used to hold the upper end of the cover cup 501, and a sound guide tube 502 is held at approximately four centimeters of the surface of the tongue in the corners of the mouth. The air exhaled by the lungs 300 passes through a pronunciation rubber piece 503 of the speech aid 500 (as shown in FIG. 11). Movement of the mouth portion speaking normally is used to emit speech sounds.

In addition, referring to FIG. 13, to improve the shortcomings of the aforementioned speech aid 500, some companies attached a gasket 600 to the front end of the cover cup 501 using glue. When the gasket 600, made from sponge, covers the new stoma 201, wearing the speech air 500 is more comfortable and will not easily leak air. However, hot water cannot be used to disinfect the sponge gasket 600, and bacteria propagate easily after a long period of usage. The gasket 600 attached using glue also easily comes apart and separates from the hard shelled cover cup 501. Furthermore, the gasket 600 on the speech aid 500 is provided with a connecting hole 601. The single size connecting hole 601 is only suitable for use with the new stoma 201 of single specifications. If the dimensions of the new stoma 201 contracts, then the connecting hole 601 of the gasket 600 is unable to seal the new stoma 201, thus limiting use thereof. Moreover, when speaking and breathing, the speech aid 500 must be taken off, and after the new stoma 201 takes in air, the speech aid 500 is then again made to cover the new stoma 201, and only then can the patient speak. Hence, for a patient suffering from a general throat malignant tumor and has undergone laryngectomy or after complete laryngectomy, then the patient must wear a tracheostomy tube. When speaking, the speech aid 500 must be positioned in line with the new stoma 201 to avoid misalignment and leak air, which makes wearing the speech aid 500 even more difficult for a new patient.

SUMMARY OF THE INVENTION

Accordingly, the primary object of the present invention is to provide an air-operated speech aid, wherein the clamp a dismountable and cleanable air gate to an inner side of a breathing hole. The air gate is able to tightly close the breathing hole when the patient is talking. When breathing and not yet speaking, the breathing hole is able to open from the inside by itself to facilitate breathing and is the same as a normal person speaking. After the patient has spoken for a period of time, saliva or phlegm will adhere to the air gate, which easily results in the propagation of bacteria. However, the dismountable air gate of the present invention can be easily disassembled for cleaning thereof, thus maintaining the sanitation and hygiene of the speech aid. Moreover, an internal tube is internally inserted into a hole at the front edge of the cover cup to accommodate different sized tracheostomy tubes. In addition, a mask type cover member is connected to one end of a sound guide tube. The cover member completely covers the mouth of the patient and eliminates the need for the sound guide tube to be inserted into the oral cavity, thereby benefiting speaking, as well as preventing saliva from flowing out, thus avoiding an unhygienic state from occurring.

To enable a further understanding of said objectives and the technological methods of the invention herein, a brief description of the drawings is provided below followed by a detailed description of the preferred embodiments.

BRIEF DESCRIPTION OF THE DRAWINGS

FIG. 2-1 shows an exploded view of an embodiment of the present invention.

FIG. 2-2 shows a schematic view of an embodiment of the present invention.

FIG. 4 shows a perspective view of another embodiment of the present invention.

FIG. 5 shows a partial schematic view of a cover cup of another embodiment of the present invention.

FIG. 6 shows a partial exploded view of a cover cup of another embodiment of the present invention.

DETAILED DESCRIPTION OF THE PREFERRED EMBODIMENTS

Figure 1:
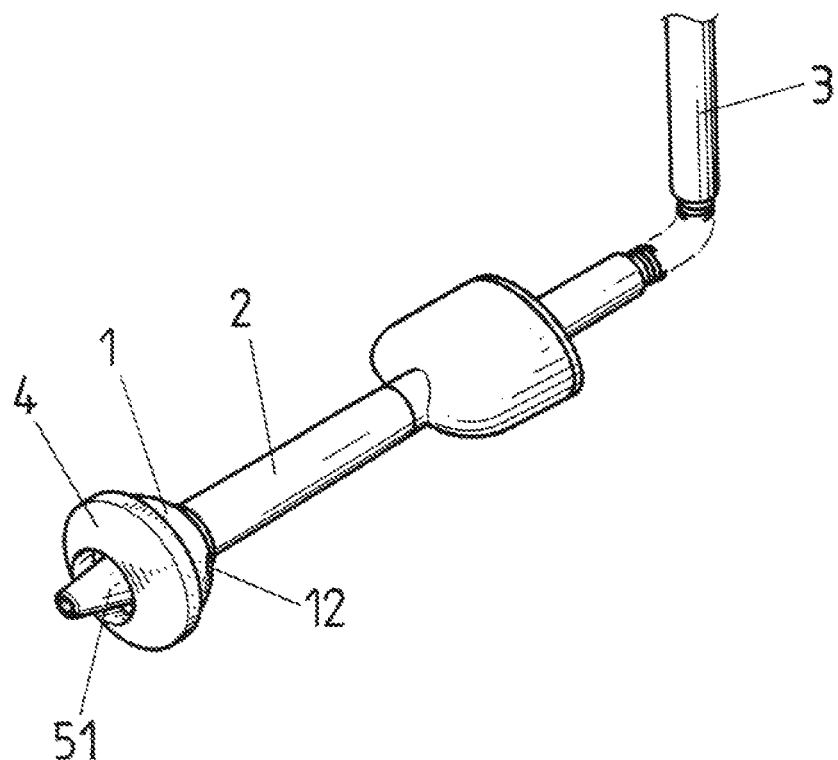
FIG. 1 shows a perspective view of the present invention.
Figure 2:
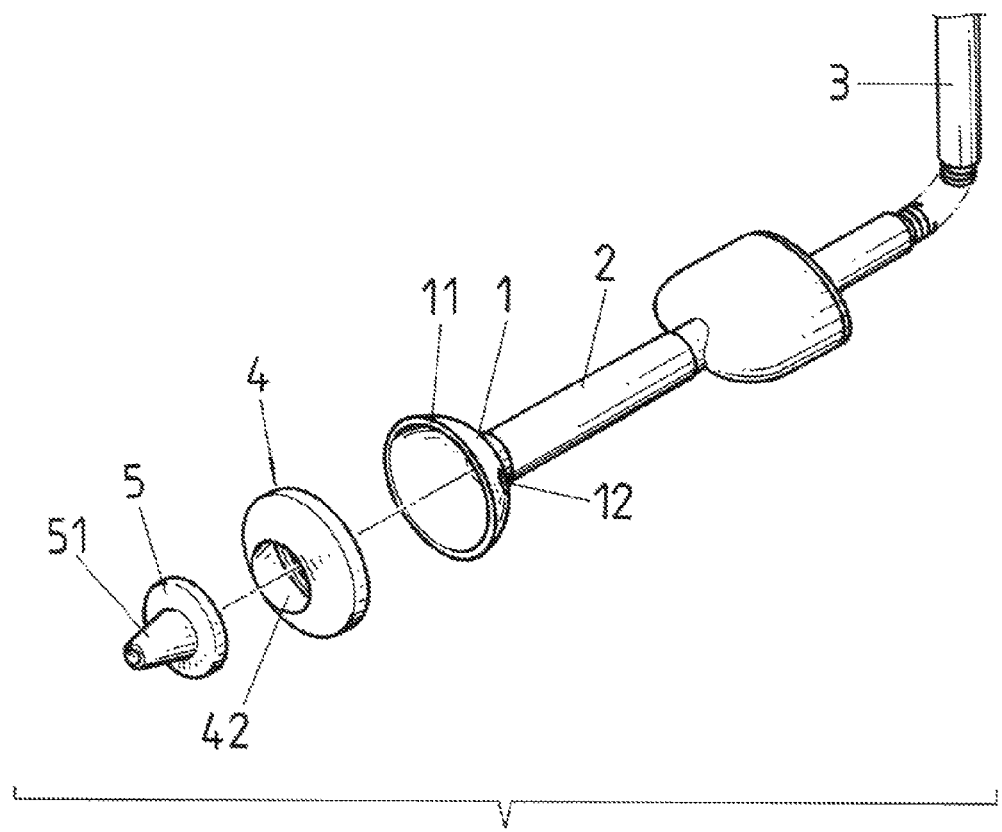
FIG. 2 shows an exploded view of the present invention.
Figure 3:
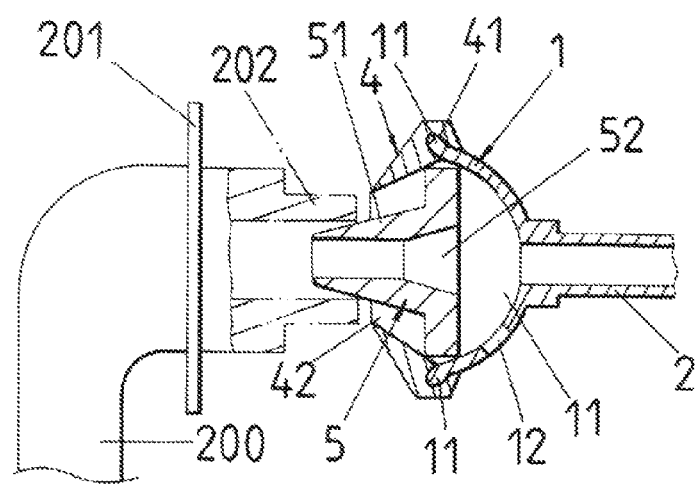
FIG. 3 shows a partial exploded view of the present invention.
Figures 1, 2:
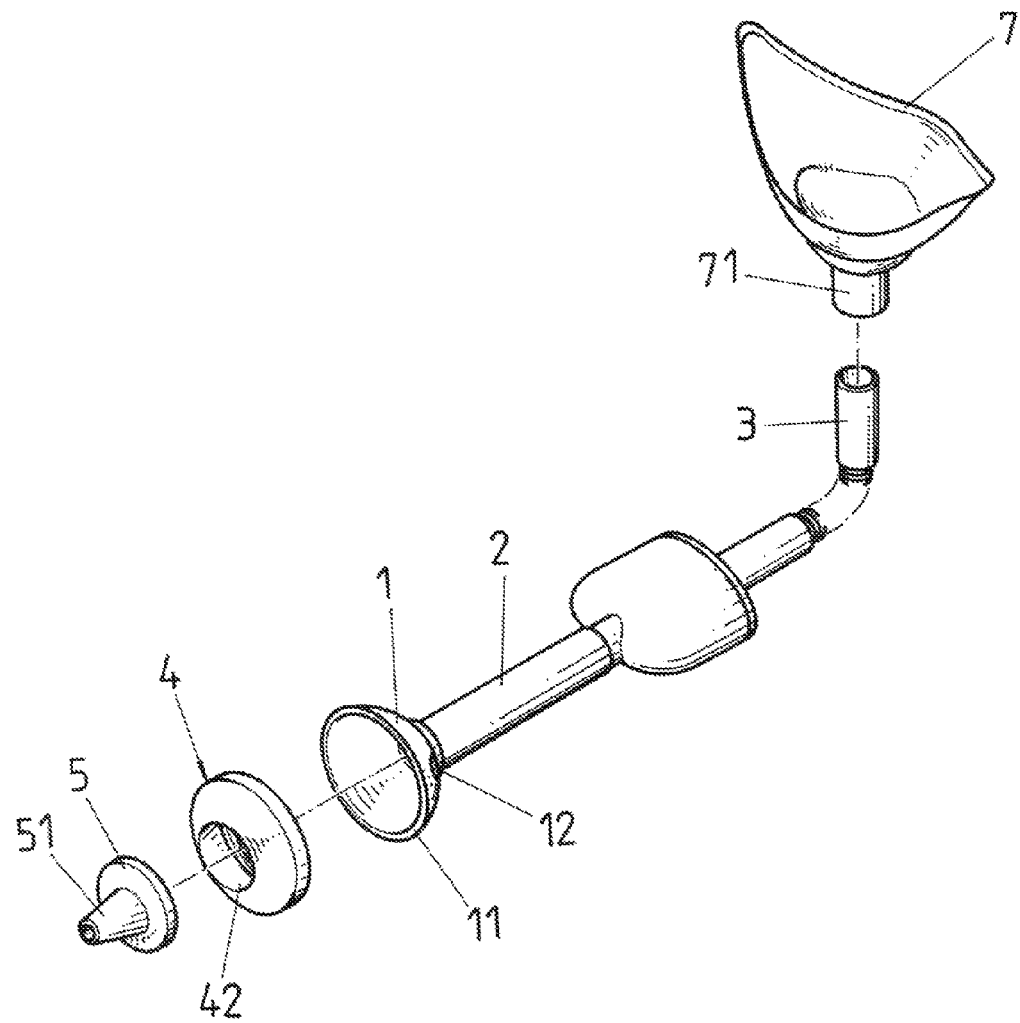
Figure 2:
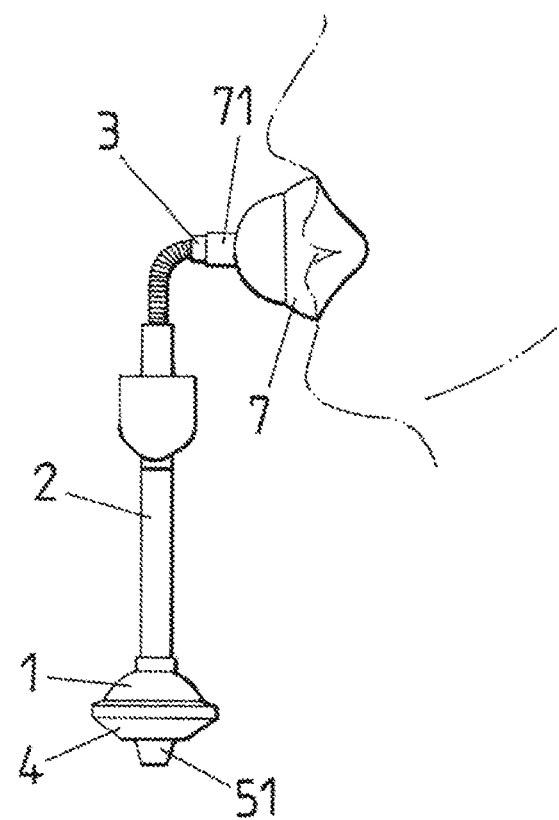
Figure 11:
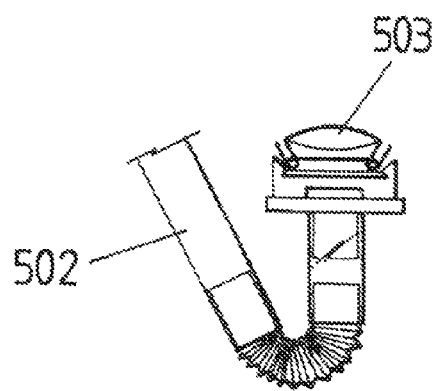
FIG. 11 shows a schematic view of the speech aid pronunciation rubber piece of the prior art.
Figure 9:
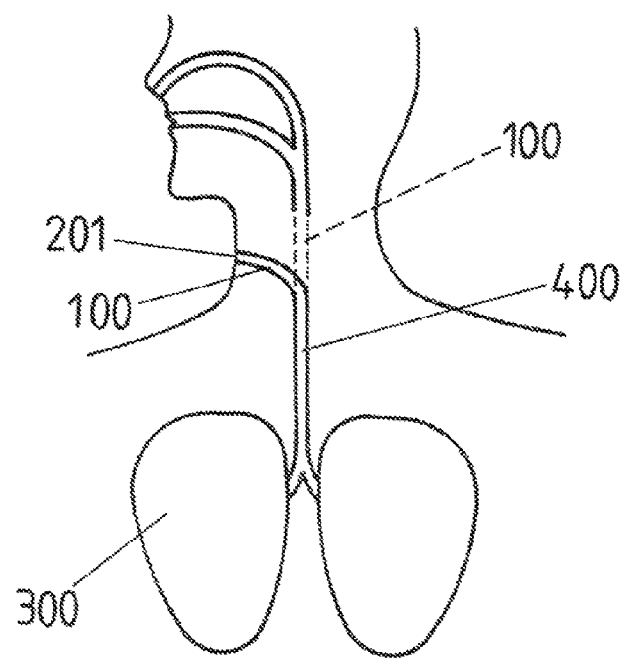
FIG. 9 shows a schematic view of human organs.
Figure 12:
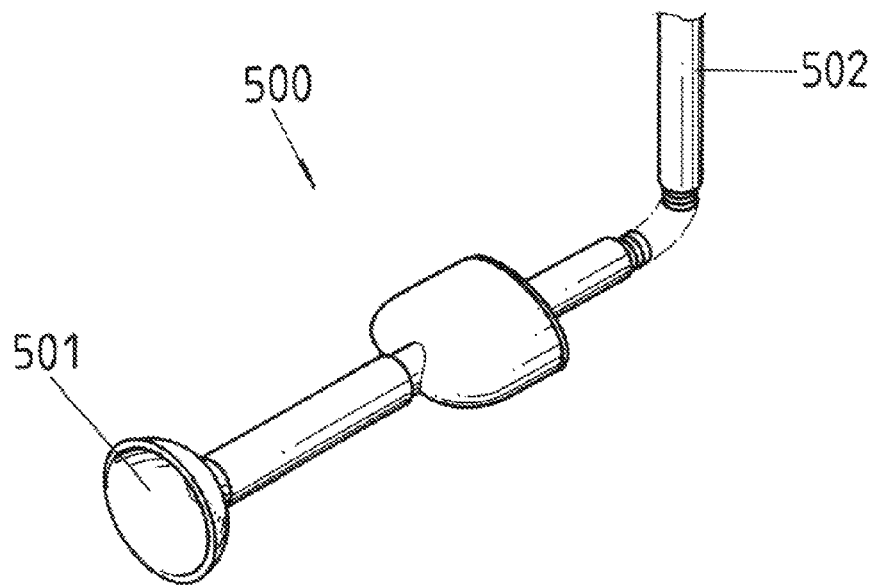
FIG. 12 shows an exterior schematic view of a speech aid of the prior art.
Figure 13:
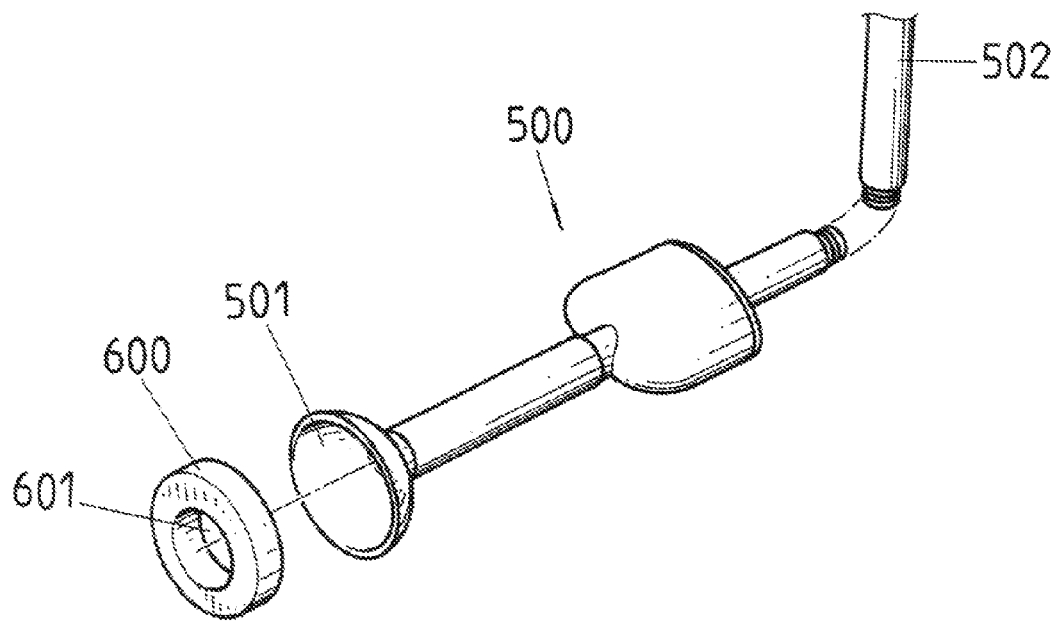
FIG. 13 shows schematic view of a gasket connected to a speech aid of the prior art.

Referring to FIGS. 1-3, the air-operated speech aid of the present invention comprises a cover cup 1, a tube 2, a sound guide tube 3, a gasket 4, and an internal tube 5. In which one end of the cover cup 1 is connected to one end of the tube 2, and the other end of the tube 2 is connected to the sound guide tube 3. The interior of the tube 2 is provided with a pronunciation rubber piece (as shown in FIG. 11). When the air exhaled by the lungs passes through the pronunciation rubber piece of the speech aid of the present invention, then the movement of the mouth portion during normal speech is used to emit speech sounds. The cover cup 1 assumes a bowl shape, and the cover cup 1 is provided with a breathing hole 12 at an appropriate position thereon. An inserting groove 41 in an inner side of one end of the conical-shaped gasket 4 enables a cup edge 11 of the the cover cup 1 to insert therein (as shown in FIG. 3), thereby fixing the gasket 4. The internal tube 5 is internally inserted into a hole 42 at the center of the gasket 4. A cone form 51 gradually tapers outward from the front edge of the internal tube 5 to facilitate tightly inserting into a connection tube 202 of a tracheostomy tube 200 penetrating a new stoma 201 (as shown in FIG. 3). Accordingly, different sizes of the connection tube 202 of the tracheostomy tube 200 can be accommodated, thus increasing the widespread usability of the product. A tube opening 52 in the inner side of the internal tube 5 assumes an outspread oblique-angled form to facilitate enabling the air exhaled by a patient to smoothly pass through the tube 2.

Referring to FIGS. 4-6, a side of the breathing hole 12 of the cover cup 1 is provided with a clasp hole 14. An air gate (or air valve) 15, made from a soft silica gel rubber, is provided with a clasp post 151, and the clasp post 151 is able to clasp inside the clasp hole 14 and fix the position of the clasp post 151 from a side direction and pointing outwards from the cover cup 1. The clasp post 151 fixes the air gate 15 at the position of the breathing hole 12. The dismountable air gate 15 can also be used to disassemble the clasp post 151 from inside the clasp hole 14. A patient who has undergone removal of lesions of the throat does not need to use the fingers to push down on the breathing hole 12 when using the speech aid to speak and breath, thus making it extremely convenient for the patient to speak with ease. When the air gate 15 has been contaminated with saliva or phlegm from the patient, the air gate 15 can be directly detached for cleaning thereof. thus maintaining cleanliness and hygiene of the speech aid.

Figure 7:
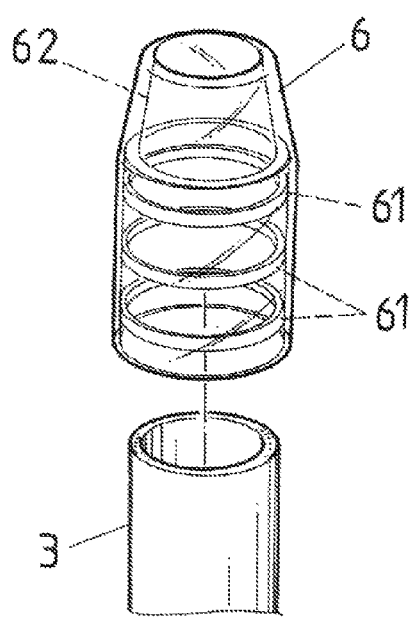
FIG. 7 shows a partial exploded view of a sound guide tube and a sleeve of the present invention.
Figure 8:
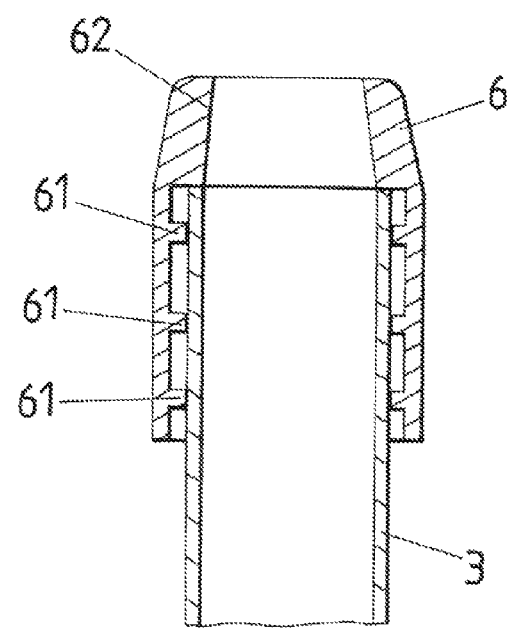
FIG. 8 shows a side view of the sleeve encased on the sound guide tube of the present invention.
Figure 10:
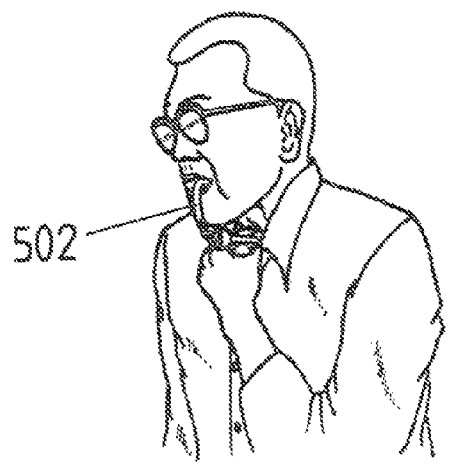
FIG. 10 shows a schematic view of a speech aid of the prior art in use.

Referring to FIG. 4, FIG. 7 and FIG. 8, a sleeve 6, made from soft silica gel, encases one end of the sound guide tube 3, and the inner side of the sleeve 6 is provided with three internal rings 61. The sleeve opening at the tail end of the sleeve 6 assumes a tapered form 62, which is used to tightly encase the sound guide tube 3 therein. When the sound guide tube 3 is extended into the mouth and placed on the tongue surface of a patient, the sound guide tube 3 will not prickle the tongue surface. Moreover, the sleeve 6 is provided with an antiskid function, which prevents the sound guide tube 3 from sliding when the patient is speaking, resulting in unclear speech.

Referring to FIG. 2-1, when the sound guide tube 3 has not yet been connected to the sleeve 6, a mask type cover member 7 can also be connected. The cover member 7 can completely cover the mouth of the patient (as shown in FIG. 2-2), and eliminates the need for the sound guide tube 3 to be inserted into the oral cavity of a patient, as well as preventing saliva from flowing out, thus avoiding an unhygienic state from occurring.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. An air-operated speech aid, comprising:
    a cover cup, the cover cup assumes a bowl shape, one end of the cover cup is provided with a cup edge, the center of an outer side of the cover cup is provided with a breathing hole, and a side of the breathing hole is provided with a clasp hole, a soft air gate is clasped within the clasp hole using a clasp post, thereby fixing the air gate at the position of the breathing hole;
    a tube, one end of the tube is connected to the cover cup, the interior of the tube is provided with a pronunciation rubber piece;
    a sound guide tube, one end of the sound guide tube is connected to one end of the tube, the other end of the sound guide tube is connected to a mask type cover member;
    a gasket, an inserting groove at one end of the gasket enables a cup edge of the cover cup to insert therein, thereby fixing the gasket, a center of the gasket is provided with a hole;
    a internal tube, the internal tube penetrates and is disposed in the hole of the gasket, a tapered form gradually tapers outward from the front edge of the internal tube, a tube opening of an inner side of the internal tube assumes an outspread oblique-angled form.

2. The air-operated speech aid according to claim 1, wherein a sleeve encases one end of the sound guide tube, the interior of the sleeve is provided with three internal rings, and the sleeve opening at the tail end of the sleeve assumes a tapered form.

* * * * *